US010555911B2

(12) United States Patent
Zhou et al.

(10) Patent No.: US 10,555,911 B2
(45) Date of Patent: Feb. 11, 2020

(54) HIGHLY PENETRATIVE NANOCARRIERS FOR TREATMENT OF CNS DISEASE

(71) Applicant: Yale University, New Haven, CT (US)

(72) Inventors: Jiangbing Zhou, Cheshire, CT (US); Toral R. Patel, Bloomfield, CT (US); Joseph M. Piepmeier, Woodbridge, CT (US); William Mark Saltzman, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 14/397,830

(22) PCT Filed: May 6, 2013

(86) PCT No.: PCT/US2013/039683
§ 371 (c)(1),
(2) Date: Oct. 29, 2014

(87) PCT Pub. No.: WO2013/166487
PCT Pub. Date: Nov. 7, 2013

(65) Prior Publication Data
US 2015/0118311 A1 Apr. 30, 2015

Related U.S. Application Data

(60) Provisional application No. 61/642,842, filed on May 4, 2012.

(51) Int. Cl.
| | | |
|---|---|---|
| *A61K 9/51* | (2006.01) | |
| *A61K 9/00* | (2006.01) | |
| *A61K 31/17* | (2006.01) | |
| *A61K 31/337* | (2006.01) | |
| *A61K 31/428* | (2006.01) | |
| *A61K 31/4745* | (2006.01) | |
| *A61K 31/495* | (2006.01) | |
| *A61K 9/19* | (2006.01) | |

(52) U.S. Cl.
CPC ............ *A61K 9/513* (2013.01); *A61K 9/0019* (2013.01); *A61K 9/0085* (2013.01); *A61K 31/17* (2013.01); *A61K 31/337* (2013.01); *A61K 31/428* (2013.01); *A61K 31/4745* (2013.01); *A61K 31/495* (2013.01); *A61K 9/19* (2013.01); *A61K 9/5153* (2013.01)

(58) Field of Classification Search
None
See application file for complete search history.

(56) References Cited

U.S. PATENT DOCUMENTS

| 4,501,726 A | 2/1985 | Schroder |
| 5,200,396 A | 4/1993 | Carenzi |
| 5,213,788 A | 5/1993 | Ranney |
| 5,302,401 A * | 4/1994 | Liversidge ............ A61K 9/146 |
| | | 424/489 |
| 6,117,454 A | 9/2000 | Kreuter |
| 6,165,440 A | 12/2000 | Esenaliev |
| 6,294,204 B1 * | 9/2001 | Rossling ............... A61K 9/1647 |
| | | 424/451 |
| 6,696,089 B2 | 2/2004 | Kabanov |
| 6,899,677 B1 * | 5/2005 | Volke et al. .................. 600/437 |
| 6,955,639 B2 | 10/2005 | Hainfeld |
| 7,025,991 B2 | 4/2006 | Sabel |
| 7,282,194 B2 | 10/2007 | Sung |
| 7,332,159 B2 | 2/2008 | Labhasetwar |
| 7,332,586 B2 | 2/2008 | Franzen |
| 8,709,483 B2 | 4/2014 | Farokhzad |
| 2003/0017131 A1 | 1/2003 | Park |
| 2004/0126379 A1 * | 7/2004 | Adolf .................... A61K 31/337 |
| | | 424/178.1 |
| 2004/0131692 A1 | 7/2004 | Kreuter |
| 2005/0226932 A1 * | 10/2005 | Yoon .................... A61K 9/0019 |
| | | 424/486 |
| 2007/0154965 A1 | 7/2007 | Zhang |
| 2007/0231360 A1 | 10/2007 | Peyman |
| 2008/0274202 A1 * | 11/2008 | Kraig .................... A61K 9/0019 |
| | | 424/491 |

(Continued)

FOREIGN PATENT DOCUMENTS

| WO | 95022963 | 3/1995 |
| WO | 98056361 | 12/1998 |

(Continued)

OTHER PUBLICATIONS

SciFinder, Dithiazanine Iodide, Retrieved online on Aug. 31, 2015.*
Murakami, Preparation of poly(DL-lactide-co-glycolide) nanoparticles by modified spontaneous emulsification solvent diffusion method, International Journal of Pharmaceutics 187 (1999) 143-152.*
Anderson, Cytotoxic Effect of Thiacarbocyanine Dyes on Human Colon Carcinoma Cells and Iniiibition of Bovine Heart Mitochondrial NADH-Ubiquinone Reductase Activity via a Rotenone-Type Mechanism by Two of the Dyes, Biochemical Pharmacology, vol. 45. No. 3. pp. 691-696. 1993.*
Chan et al., PLGA-lecithin-PEG core-shell nanoparticles for controlled drug delivery, Biomaterials 30 (2009) 1627-1634.*

(Continued)

*Primary Examiner* — Jennifer A Berrios
(74) *Attorney, Agent, or Firm* — Pabst Patent Group LLP

(57) ABSTRACT

Brain-penetrating polymeric nanoparticles that can be loaded with drugs and are optimized for intracranial convection-enhanced delivery (CED) have been developed. In the preferred embodiment, these are loaded with FDA-approved compounds, identified through library screening to target brain cancer stem cells (BSCSs). The particles are formed by emulsifying a polymer-drug solution, then removing solvent and centrifuging at a first force to remove the larger particles, then collecting the smaller particles using a second higher force to sediment the smaller particles having a diameter of less than 100 nm, more preferably less than 90 nanometers average diameter, able to penetrate brain interstitial spaces.

17 Claims, 5 Drawing Sheets

(56) References Cited

U.S. PATENT DOCUMENTS

| | | | | |
|---|---|---|---|---|
| 2010/0216804 | A1* | 8/2010 | Zale | A61K 9/0019 514/249 |
| 2011/0021592 | A1* | 1/2011 | Magdassi | A61K 9/1075 514/406 |
| 2011/0064794 | A1* | 3/2011 | Deng | A61K 9/1075 424/450 |

FOREIGN PATENT DOCUMENTS

| | | |
|---|---|---|
| WO | 2005063210 | 7/2005 |
| WO | 2005120469 | 12/2005 |
| WO | 2006029845 | 3/2006 |
| WO | 2006044660 | 5/2006 |
| WO | 2006096499 | 9/2006 |
| WO | 2006102377 | 9/2006 |
| WO | 2007016501 | 2/2007 |
| WO | 2007088066 | 8/2007 |
| WO | 2007110152 | 10/2007 |
| WO | 2008024753 | 2/2008 |
| WO | WO2008122035 | * 10/2008 |
| WO | 2012101639 | 8/2012 |

OTHER PUBLICATIONS

Abbott, "Cancer: the root of the problem", Nature, 442:742-3 (2006).
Allard, et al., "Convection-enhanced delivery of nanocarriers for the treatment of brain tumors", Biomaterials, 30:2302-18 (2009).
Bao, et al., "Stem cell-like glioma cells promote tumor angiogenesis through vascular endothelial growth factor", Cancer Res., 66:7843-8 (2006a).
Bao, et al., "Glioma stem cells promote radioresistance by preferential activation of the DNA damage response", Nature, 444:756-60 (2006b).
Beier, et al., "CD133(+) and CD133(−) glioblastoma-derived cancer stem cells show differential growth characteristics and molecular profiles", Cancer Res., 67:4010-5 (2007).
Bobo, et al., "Convection-enhanced delivery of macromolecules in the brain", PNAS, 91:2076-80 (1994).
Brem, et al., "Interstitial chemotherapy with drug polymer implants for the treatment of recurrent gliomas", J Neurosurg., 74:441-6 (1991).
Brem, et al., "Placebo-controlled trial of safety and efficacy of intraoperative controlled delivery by biodegradable polymers of chemotherapy for recurrent gliomas. The Polymer-brain Tumor Treatment Group", Lancet, ,345:1005-12 (1995).
Calabrese, et al., "A perivascular niche for brain tumor stem cells", Cancer Cell, 11:69-82 (2007).
Chen, et al., "Surface properties, more than size, limiting convective distribution of virus-sized particles and viruses in the central nervous system", J Neurosurg., 103:311-9 (2005).
Chong, et al., "A clinical drug library screen identifies astemizole as an antimalarial agent", Nature Chem Biol., 2:415-6 (2006).
Clarke, "Neurobiology: at the root of brain cancer", Nature, 432:281-2 (2004).
Eramo, et al., "Chemotherapy resistance of glioblastoma stem cells", Cell Death Differ., 13:1238-41 (2006).
Fan, et al., "Glioma stem cells: evidence and limitation", Semin Cancer Biol., 17:214-8 (2007).
Fung, et al., "Pharmacokinetics of interstitial delivery of carmustine, 4-hydroperoxycyclophosphamide, and paclitaxel from a biodegradable polymer implant in the monkey brain", Cancer Res., 58:672-84 (1998).
Fung, et al., "Chemotherapeutic drugs released from polymers: distribution of 1,3-bis(2-chloroethyl)-1-nitrosourea in the rat brain", Pharm Res., 13:671-82 (1996).
Galli, et al., "Isolation and characterization of tumorigenic, stem-like neural precursors from human glioblastoma", Cancer Res., 64:7011-21 (2004).
Gaumet, et al., "Nanoparticles for drug delivery: The need for precision in reporting particle size parameters", EU J Pharma Biopharma.,69(1):1-9 (2008).
Gunther, et al., "Glioblastoma-derived stem cell-enriched cultures form distinct subgroups according to molecular and phenotypic criteria", Oncogene, 27:2897-909 (2008).
Hirschmann-Jax, et al., "A distinct "side population" of cells with high drug efflux capacity in human tumor cells", PNAS, 101(39):14228-33 (2004).
Hobbs, et al., "Regulation of transport pathways in tumor vessels: role of tumor type and microenvironment", PNAS, 95:4607-12 (1998).
Hochberg, et al., "Assumptions in the radiotherapy of glioblastoma", Neurology, 30:907-11 (1980).
Jacobs, et al., "Positron-emission tomography of vector-mediated gene expression in gene therapy for gliomas", Lancet, 358:727-9 (2001).
Jones, et al., "Cancer stem cells: are we missing the target", J Natl Cancer Inst., 96:583-5 (2004).
Kreuter, "Nanoparticulate systems for brain delivery of drugs", Adv Drug Deliv Rev., 47:65-81 (2001).
Kunwar, et al., "Phase III randomized trial of CED of IL13-PE38QQR vs Gliadel wafers for recurrent glioblastoma", Neuro Oncol., 12:871-81 (2010).
Liu, et al., "Analysis of gene expression and chemoresistance of CD133+ cancer stem cells in glioblastoma", Mol Cancer ,5:67 (2006).
Mamot, et al., "Extensive distribution of liposomes in rodent brains and brain tumors following concection-enhanced delivery", J Neuro Oncol., 68(1):1-9 (2004).
Mrugala, et al., "Mechanisms of disease: temozolomide and glioblastoma—look to the future", Nat Clin Pract Oncol., 5:476-86 (2008).
Musumeci, et al., "Lyoprotected nanosphere formalations for paclitaxel controlled delivery",J NanoSci Nanotech., 6:3118-25 (2006).
Neeves, et al., "Dilation and degradation of the brain extracellular matrix enhances penetration of infused polymer nanoparticles", Brain Res., 1180:121-32 (2007).
Reya, et al., "Stem cells, cancer, and cancer stem cells", Nature, 414:105-11 (2001).
Sampson, et al., "Poor drug distribution as a possible explanation for the results of the PRECISE trial", J.neurosurg , 113:301-9 (2010).
Sampson, et al., "Intracerebral infusion of an EGFR-targeted toxin in recurrent malignant brain tumors", Neuro Oncol., 10:320-9 (2008).
Sawyer, et al., "Convection-enhanced delivery of camptothecin-loaded polymer nanoparticles for treatment of intracranial tumors", Drug Deliv Transl Res., 1:34-42 (2011).
Sawyer, et al., "New methods for direct delivery of chemotherapy for treating brain tumors", Yale J Biol Med:, 79:141-52 (2006).
Singh, et al., "Identification of a cancer stem cell in human brain tumors", Cancer Res., 63:5821-8 (2003).
Singh, et al., "Identification of human brain tumor initiating cells", Nature, 432:396-401 (2004).
Stupp, et al., "Radiotherapy plus concomitant and adjuvant temozolomide for glioblastoma", N Engl J Med., 352:987-96 (2005).
Stupp, et al., "Effects of radiotherapy with concomitant and adjuvant temozolomide versus radiotherapy alone on survival in glioblastoma in a randomised phase III study: 5-year analysis of the EORTC-NCIC trial", Lancet Oncology, 10:459-66 (2009).
Tang, et al., "Insights into the cancer stem cell model of glioma tumorigenesis". Ann Acad Med Singapore, 36:352-7 (2007).
Thorne, et al., "In vivo diffusion analysis with quantum dots and dextrans predicts the width of brain extracellular space", PNAS,. 103:5567-72 (2006).
Yuan, et al., "Isolation of cancer stem cells from adult glioblastoma multiforme", Oncogene. 23:9392-9400 (2004).
Zheng, et al., "[18F]PEG-Biotin labeled nanoparticles for tracking drug delivery and tumor therapy", J. Nuclear Med., 52Supp:417 (2011).

(56) References Cited

OTHER PUBLICATIONS

Anhorn, et al., "Freeze drying of human serum albumin (HAS) nanoparticles with different excipients", Intl J Pharmaceutics, 363:162-9 (2008).
Bisht, et al., "Polymeric nanoparticle-encapsulated curcumin ("nanocurcumin"): A novel strategy for human cancer therapy", J Nanobiotechnology, 5(3):1-14 (2007).
Chopra, et al., "Brain permeable nanoparticles", Recent Patents on CNS Drug Discovery, 3:216-25 (2008).
Corrigan and Li, "Quantifying drug release from PLGA nanoparticulates", Eu J Pharma Scie., 37:477-85 (2009).
Debinski and Tatter, "Convection-enhanced delivery for the treatment of brain tumors", Expert Rev Neurother, 9(10):1519-27 (2009).
Hollmer, "Novel nanoparticles penetrate fruit flies\ brains; people\s may be next", Fierce Drug Delivery, http://www.fiercedrugdelivery.com/story/novel-nanoparticles-penetrate-fruitflies-brains-next-people/ 2012-01-09., weekly newsletter for Jan. 9, 2012.
Huang, et a., "Enhanced gene transfer into brain capillary endothelial cells using Antp-modified DNA-loaded nanoparticles", J Biomed Sci., 14(5):595-605 (2007).
Kim, et al. "Translocation of poly(ethylene glycol-co-hexadecyl)cyanoacrylate nanoparticles into rat brain endothelial cells: role of apolipoproteins in receptor-mediated endocytosis", Biomacromolecules, 8(3): 793.9 (2007).
Kocbek, et al., "Preparation and evaluation of nanosuspensions for enhancing the dissolution of poorly soluble drugs", Intl J Pharm, 312:179-86 (2006).
Koffie, et al., "Nanoparticles enhance brain delivery of blood-brain barrier-impermeable probes for in vivo optical and magnetic resonance imaging", PNAS, 108(46):18837-42 (2011).
Konan, et al., "Preparation and characterization of sterile and freeze-dried sub-200 nm nanoparticles", Intl. J Pharmaceutics, 233:239-52 (2003).
Levin, et al., "Sucrose and insulin space measurements of cerebral cortex in four mammalian species", Am J Physiol,, 219:1528-33 (1970).
Mohanraj and Chen, "Nanoparticles—A review", Tropical J Phaema Res., 5 (1):56173 (2006).
Nicholson, et al., "Extracellular space structure revealed by diffusion analysis", Trends Neurosci., 21:207-15 (1998).
Patel, et al., "Polymeric nanoparticles for drug delivery to the central nervous system", Adv. Drug Deliv Rev., 64(7):701-5 (2011).
Price, et al., "Delivery of brain tumor penetrating nanoparticles across the blood-brain barrier with MRgFUS", http://www.fusfoundation.org/Funded-Projects/delivery-of-brain-tumor, 3 pages, retrieved from the internet Feb. 7, 2012.
Proudfoot-Jones and Leung, "Nanotechnology breakthrough: Penetration of the blood brain barrier for the treatment of Parkinson\s disease", Research paper based on pathology lectures at Medlink (2010).
Saito, et al., "Tissue affinity of the infusate affects the distribution volume during convection-enhanced delivery into rodent brains: implications for local drug delivery", J Neursci Methods, 154:226-32 (2006).
Science Daily, "Nanoparticles cross blood-brain battier to enable brain tumor painting", http://www.sciencedaily.com/releases/2009/08/09080318574.htm, 3 pages, retrieved from the internet Feb. 8, 2012.
Skyova, et al., "Diffusion in brain extracellular space", Physicol Rev., 88:1277-1340 (2008).
Trotta, et al., "Emulsions containing partially water-miscible solvents for the preparation of drug nanosuspensions", J Control Rel., 76(1-2):119-28 (2001).
Xia, et al., "Low molecular weight protamine-functionalized nanoparticles for drug delivery to the brain after intranasal administration", Biomaterials, 32(36):988-98 (2011).
Xia, et al., "Nanoparticulate formulations for paclitaxel delivery across MDCK cell monolayer", Curr Pharm Des., 16(21):2331-40 (2010).
Zhou, et al., "Novel delivery strategies for glioblastoma", Cancer, 15 (1)::doi:10.1097/PPO.0b013e318244d8ae (2012).

\* cited by examiner

Supplemental Table 1. $IC_{50}$ (µM) of candidate drugs on GS5 cells

|    | Compound name | $IC_{50}$ |    | Compound name | $IC_{50}$ |
|----|---------------|-----------|----|---------------|-----------|
| 1  | Quinacrine | 2.7 | 17 | Hydroxocobalamin hydrochloride | 32.1 |
| 2  | Acriflavine hydrochloride | 3.0 | 18 | Glycocyamine | 33.9 |
| 3  | Cytarabine | 0.8 | 19 | Calcium propionate | 29.5 |
| 4  | 8-Hydroxyquinidine | 2.7 | 20 | Miltefosine | 27.8 |
| 5  | Digoxin | 0.3 | 21 | Emetine | 0.3 |
| 6  | Dithiazanine iodide | 0.3 | 22 | Cladribine | 3.4 |
| 7  | Neocuproine | 0.2 | 23 | Saponin | 8.9 |
| 8  | Anisomycin | 0.3 | 24 | Parthenolide | 3.0 |
| 9  | PAPP | 0.9 | 25 | Bromocriptine | 9.1 |
| 10 | Betamethasone | 25.9 | 26 | Hycanthone | 5.6 |
| 11 | Chlorpheniramine | 40.4 | 27 | Prochlorperazine dimaleate | 5.6 |
| 12 | Proscillaridin A | 0.1 | 28 | Astemizole | 3.2 |
| 13 | Falnidamol | 22.0 | 29 | Harmine | 19.3 |
| 14 | 8-Quinolinol hemisulfate | 3.0 | 30 | Cephradine | 38.5 |
| 15 | Ammonium pyrrolidinedithiocarbamate | 3.3 | 31 | Thioguanine | 4.6 |
| 16 | Iron(II) sulfate heptahydrate | 32.1 | 32 | 6-Mercaptopurine monohydrate | 7.8 |

FIG. 3B

HIGHLY PENETRATIVE NANOCARRIERS FOR TREATMENT OF CNS DISEASE

CROSS REFERENCE TO RELATED APPLICATIONS

This application is a 371 application of International Application No. PCT/US2013/039683, filed May 6, 2013, which claims the benefit of and priority to U.S. Provisional Application No. 61/642,842, filed May 4, 2012.

STATEMENT REGARDING FEDERALLY SPONSORED RESEARCH OR DEVELOPMENT

This invention was made with government support under grant CA149128 awarded by the National Institutes of Health. The government has certain rights in the invention.

FIELD OF THE INVENTION

This application is generally in the field of drug delivery, and more specifically delivery of chemotherapeutics to the brain, especially for the treatment of glioblastoma.

BACKGROUND OF THE INVENTION

Of the approximately 40,000 people diagnosed with primary brain tumors in the United States each year, an estimated 15,000 have glioblastoma multiforme (GBM), a WHO grade IV malignant glioma (Mrugala, et al Nat Clin Pract Oncol 5, 476-486 (2008)). Despite considerable research efforts, the prognosis for GBM remains poor: median survival with standard-of-care therapy (surgery, systemic chemotherapy with temozolomide, and radiation) is 14.6 months (Stupp et al., N Engl J Med 352, 987-996 (2005)) and five-year survival is 9.8% (Stupp et al., The lancet oncology 10, 459-466 (2009)), with the vast majority of GBMs recurring within 2 cm of the original tumor focus (Hochberg, et al. Neurology 30, 907-911 (1980)). Histopathologically, GBM is characterized by its infiltrative nature and cellular heterogeneity, leading to a number of challenges that must be overcome by any presumptive therapy.

The blood-brain barrier (BBB) is a major obstacle to treating GBM (J. Kreuter, Adv Drug Deliv Rev 47, 65-81 (2001)). Clinical trials have demonstrated that the BBB can be safely bypassed with direct, locoregional delivery of therapeutic agents. For example, local implantation of a drug-loaded biodegradable polymer wafer (presently marketed as Gliadel®), which slowly releases carmustine (BCNU) over a prolonged period, is a safe and effective method for treating GBM. However, use of the Gliadel® wafer results in only modest improvements in patient survival, typically two months. (H. Brem et al., J Neurosurg 74, 441-446 (1991); H. Brem et al., Lancet 345, 1008-1012 (1995)). These wafers produce high interstitial drug concentrations in the tissue near the implant, but because drugs move from the implant into the tissue by diffusion—penetration into tissue is limited to approximately 1 mm, which could limit their efficacy (Fung, et al. Pharm Res 13, 671-682 (1996); Fung et al., Cancer Res 58, 672-684 (1998)).

Drug developers have long been frustrated by the BBB, which severely limits the types of agents that can be tested for activity in the brain. Current therapy for glioblastoma multiforma (GBM) is insufficient, with nearly universal recurrence. Available drug therapies are unsuccessful because they fail to penetrate through the region of the brain containing tumor cells and they fail to kill the cells most responsible for tumor development and therapy resistance, brain cancer stem cells (BCSCs).

Convection-enhanced delivery (CED), in which agents are infused into the brain under a positive pressure gradient, creating bulk fluid movement in the brain interstitium (Bobo et al., Proc Natl Acad Sci USA 91, 2076-2080 (1994)) is safe and feasible (S. Kunwar et al., Neuro Oncol 12, 871-881 (2010); J. H. Sampson et al., Neuro Oncol 10, 320-329 (2008); A. Jacobs et al., Lancet 358, 727-729 (2001)), but CED alone is not sufficient to improve GBM treatment. For example, CED of a targeted toxin in aqueous suspension failed to show survival advantages over Gliadel® wafers (Kunwar et al., Neuro Oncol 12, 871-881 (2010); Sampson et al., J. neurosurg. 113, 301-309 (2010)). While CED of drugs in solution results in increased penetration, most drugs have short half-lives in the brain and, as a result, they disappear soon after the infusion stops Sampson et al (2010); Allard, et al. Biomaterials 30, 2302-2318 (2009). Loading of agents into nanocarriers, such as liposomes, micelles, dendrimers, or nanoparticles, can protect them from clearance. Compared to other carriers, nanoparticles made from the FDA-approved poly(lactide-co-glycolide) (PLGA) are stable, safe, and tunable to control drug release. But CED of PLGA nanoparticles, which are typically 100-200 nm in diameter, has been limited by the failure of particles to move by convection through the brain interstitial spaces (Sawyer, et al. Yale J Biol Med 79, 141-152 (2006); Sawyer et al., Drug Deliv Transl Res 1, 34-42 (2011); Neeves, et al. Brain Res 1180, 121-132 (2007); Chen et al., J Neurosurg 103, 311-319 (2005), which appear to be 38-64 nm in normal brain (Thorne, et al. Proc Natl Acad Sci USA 103, 5567-5572 (2006)) and 7-100 nm in regions with tumor (Hobbs et al., Proc Natl Acad Sci U SA 95, 4607-4612 (1998)).

It is therefore an object of the present invention to provide drug carriers which can penetrate into both normal and cancerous brain interstitial spaces and provide prolonged release of therapeutic agents.

SUMMARY OF THE INVENTION

Brain-penetrating polymeric nanoparticles that can be loaded with drugs and are optimized for intracranial convection-enhanced delivery (CED) have been developed. In the preferred embodiment, these are loaded with FDA-approved compounds, identified through library screening to target brain cancer stem cells (BSCSs). The particles are formed by emulsifying a polymer-drug solution, then removing solvent and centrifuging at a first force to remove the larger particles, then collecting the smaller particles using a second higher force to sediment the smaller particles having a diameter of less than 100 nm, more preferably in the range of 25-75 nanometers average diameter, able to penetrate brain interstitial spaces.

Using fluorescence imaging and positron emission tomography (PET), it was demonstrated that brain-penetrating nanoparticles can be delivered intracranially to large volumes in both rat and pig. Several FDA-approved agents that potently inhibit proliferation and self-renewal of BCSCs were tested. When loaded into brain-penetrating nanoparticles and administered by convection-enhanced delivery (CED), one of these agents, dithiazanine iodide (DI), significantly increased survival in rats bearing BCSC-derived xenografts. Other preferred active agents include Carmustine (BCNU), temozolomide, paclitaxel, and camptothecin.

Treatment of brain tumors is improved by 1) enhancing the depth of penetration of locally-delivered therapeutic agents using convection-enhanced delivery (CED), in which agents are infused into the brain under a positive pressure gradient, creating bulk fluid movement in the brain interstitium (Bobo et al., Proc Natl Acad Sci USA 91, 2076-2080 (1994), 2) providing for long-term release of active agents using polymer nanocarriers that are much smaller than conventional particles and still capable of efficient drug loading and controlled release, and 3) delivering agents that are known to be effective against the cells that are most important in tumor recurrence. Reliable methods for making PLGA nanoparticles with these characteristics have been developed that enable direct testing of novel agents that address the complexity of GBM biology.

BRIEF DESCRIPTION OF THE DRAWINGS

FIG. 2A is a graph of the in vitro evaluation of digoxin on BCSCs, showing that digoxin treatment inhibited BCSC proliferation. Treatment with digoxin at 1 or 5 µM inhibited BCSC sphere formation. Treatment with digoxin at 1 µM decreased the CD133+ population in the BCSC line PS11, as determined by flow cytometry. Characteristics, including morphology, size distribution and controlled release profile (FIG. 2B) of brain-penetrating nanoparticles loaded with digoxin were measured. FIG. 2C is a graph of Kaplan-Meier survival curves for tumor-bearing rats with indicated treatments: black line, no treatment (n=6); red line, control NPs (n=6); green line, brain-penetrating digoxin NPs (n=6).

FIGS. 3A and 3B are tables of compounds screened for inhibition of GS5 sphere formation.

DETAILED DESCRIPTION OF THE INVENTION

Figure 1A:
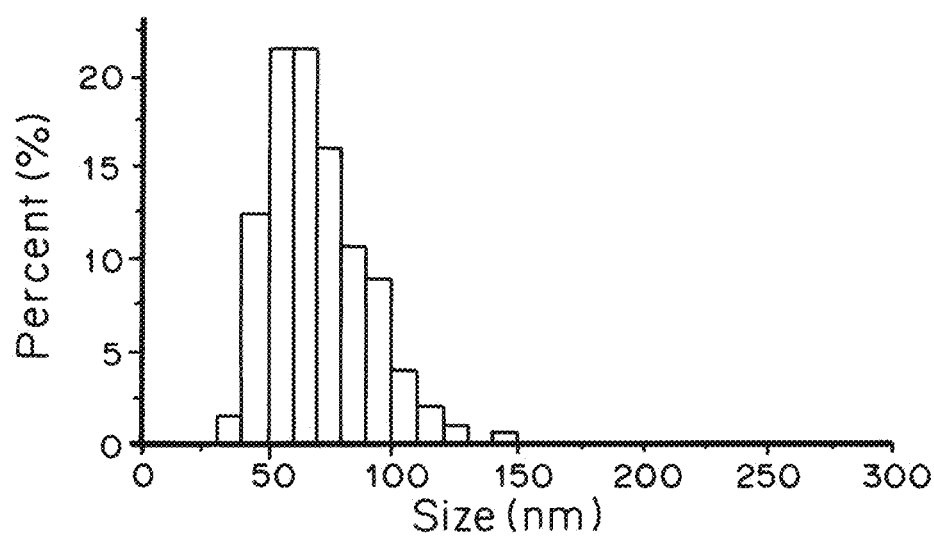
FIGS. 1A, 1B and 1C are graphs of the synthesis and antitumor effects of nanoparticle-encapsulated DI on BCSC xenograft tumors in the rat. Size distribution (FIG. 1A), controlled release profile of small DI-loaded nanoparticles (NPs) (FIG. 1B), Kaplan-Meier survival curves for tumor-bearing rats with indicated treatments: blue line, brain-penetrating DI NPs (median survival >280 d); red line, standard DI NPs (median survival 180 d); green line, free DI (median survival 177 d); yellow line, blank NPs (median survival 156 d); grey line, no treatment (median survival 147 d) (FIG. 1C). Rats treated with brain-penetrating, DI-loaded NPs had significant improvements in median survival compared to all other groups (p<0.005 for each comparison). The experiment shown in FIG. 1C has been repeated, on separate occasions, with similar results.

The creation of safe, versatile, brain-penetrating nanocarriers enables direct testing of agents that address the complexity of GBM biology. Cells isolated from distinct regions of a given GBM bear grossly different expression signatures, but appear to arise from a common progenitor. A small subpopulation of these progenitors drives tumor progression, promotes angiogenesis, and influences tumor cell migration (Fan, et al Semin Cancer Biol 17, 214-218 (2007); M. F. Clarke, Nature 432, 281-282 (2004); S. Bao et al., Nature 444, 756-760 (2006); C. Calabrese et al., Cancer Cell 11, 69-82 (2007)). These cells have features of primitive neural stem cells and, as a result, are called brain cancer stem cells (BCSCs) (S. Bao et al., Nature 444, 756-760 (2006); S. K. Singh et al., Cancer Res 63, 5821-5828 (2003); R. Galli et al., Cancer Res 64, 7011-7021 (2004); S. K. Singh et al., Nature 432, 396-401 (2004); X. Yuan et al., Oncogene 23, 9392-9400 (2004); S. Bao et al., Cancer Res 66, 7843-7848 (2006); D. Beier et al., Cancer Res 67, 4010-4015 (2007); H. S. Gunther et al., Oncogene, (2007). BCSCs, many of which are marked by CD133 (PROM1), are resistant to conventional drugs (M. F. Clarke, Nature 432, 281-282 (2004); R. J. Jones, J Natl Cancer Inst 96, 583-585 (2004)), including carboplatin, cisplatin, paclitaxel, doxorubicin, vincristine, methotrexate, and temozolomide (Tang, et al. Ann Acad Med Singapore 36, 352-357 (2007); G. Liu et al., Mol Cancer 5, 67 (2006); A. Eramo et al., Cell Death Differ 13, 1238-1241 (2006); C. Hirschmann-Jax et al., Proc Natl Acad Sci USA 101, 14228-14233 (2004)), as well as radiotherapy (S. Bao et al., Nature 444, 756-760 (2006)). These observations suggest that agents that target BCSCs are more likely to lead to cure of GBM (M. F. Clarke, Nature 432, 281-282 (2004); Jones, J Natl Cancer Inst 96, 583-585 (2004); A. Abbott, Cancer: the root of the problem. Nature 442, 742-743 (2006); Reya, et al. Nature 414, 105-111 (2001).

I. Definitions

The term "biocompatible" as used herein refers to one or more materials that are neither themselves toxic to the host (e.g., an animal or human), nor degrade (if the material degrades) at a rate that produces monomeric or oligomeric subunits or other byproducts at toxic concentrations in the host. The term "biodegradable" as used herein means that the materials degrades or breaks down into its component subunits, or digestion, e.g., by a biochemical process, of the material into smaller (e.g., non-polymeric) subunits.

"Sustained release" as used herein refers to release of a substance over an extended period of time in contrast to a bolus type administration in which the entire amount of the substance is made biologically available at one time.

The term "microspheres" is art-recognized, and includes substantially spherical colloidal structures formed from biocompatible polymers having a size ranging from about one or greater up to about 1000 microns. In general, "microcapsules," also an art-recognized term, may be distinguished from microspheres, as formed of a core and shell. The term "microparticles" is also art-recognized, and includes microspheres and microcapsules, as well as structures that may not be readily placed into either of the above two categories, all with dimensions on average of less than about 1000 microns. If the structures are less than about one micron in diameter, then the corresponding art-recognized terms "nanosphere," "nanocapsule," and "nanoparticle" may be utilized. In certain embodiments, the nanospheres, nanocapsules and nanoparticles have an average diameter of about 500 nm, 200 nm, 100 nm, 50 nm, 10 nm, or 1 nm.

A composition containing microparticles or nanoparticles may include particles of a range of particle sizes. In certain embodiments, the particle size distribution may be uniform, e.g., within less than about a 20% standard deviation of the mean volume diameter, and in other embodiments, still more uniform, e.g., within about 10% of the median volume diameter.

The term "particle" as used herein refers to any particle formed of, having attached thereon or thereto, or incorporating a therapeutic, diagnostic or prophylactic agent.

The term "targeting moiety" as used herein refers to a moiety that localizes to or away from a specific locale. The moiety may be, for example, a protein, nucleic acid, nucleic acid analog, carbohydrate, or small molecule. Said entity may be, for example, a therapeutic compound such as a small molecule, or a diagnostic entity such as a detectable label. Said locale may be a tissue, a particular cell type, or a subcellular compartment. In one embodiment, the targeting moiety directs the localization of an active entity. The active entity may be a small molecule, protein, polymer, or metal. The active entity may be useful for therapeutic, prophylactic, or diagnostic purposes.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The term "pharmaceutically acceptable salts" is art-recognized, and includes relatively non-toxic, inorganic and organic acid addition salts of compounds. Examples of pharmaceutically acceptable salts include those derived from mineral acids, such as hydrochloric acid and sulfuric acid, and those derived from organic acids, such as ethanesulfonic acid, benzenesulfonic acid, and p-toluenesulfonic acid. Examples of suitable inorganic bases for the formation of salts include the hydroxides, carbonates, and bicarbonates of ammonia, sodium, lithium, potassium, calcium, magnesium, aluminum, and zinc. Salts may also be formed with suitable organic bases, including those that are non-toxic and strong enough to form such salts.

The term "treating" preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The term "therapeutically effective amount" refers to an amount of the therapeutic agent that, when incorporated into and/or onto particles described herein, produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation. In some embodiments, the term "effective amount" refers to an amount of a therapeutic agent or prophylactic agent to reduce or diminish the symptoms of one or more diseases or disorders of the brain, such as reducing tumor size (e.g., tumor volume) or reducing or diminishing one or more symptoms of a neurological disorder, such as memory or learning deficit, tremors or shakes, etc. In still other embodiments, an "effective amount" refers to the amount of a therapeutic agent necessary to repair damaged neurons and/or induce regeneration of neurons.

The terms "incorporated" and "encapsulated" refers to incorporating, formulating, or otherwise including an active agent into and/or onto a composition that allows for release, such as sustained release, of such agent in the desired application. The terms contemplate any manner by which a therapeutic agent or other material is incorporated into a polymer matrix, including for example: attached to a monomer of such polymer (by covalent, ionic, or other binding interaction), physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions), encapsulated inside the polymeric matrix, etc. The polymer can be a hydrophobic biodegradable polymer. The term "co-incorporation" or "co-encapsulation" refers to-the incorporation of a therapeutic agent or other material and at least one other therapeutic agent or other material in a subject composition.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer that it is dispersed as small droplets, rather than being dissolved, in the polymer.

II. Polymeric Nanoparticle Compositions

A. Polymeric Nanoparticles.

Suitable polymeric carriers include, but are not limited to poly(lactic acid) (PLA), poly(lactic-co-glycolic acid) (PLGA), poly(lactic acid)-polyethyleneglycol (PLA-PEG) block copolymers, polyanhydrides, poly(ester anhydrides), ppolyglycolide (PGA), poly-3-hydroxybutyrate (PHB) and copolymers thereof, poly-4-hydroxybutyrate (P4HB), polycaprolactone, cellulose, hydroxypropyl methylcellulose, ethylcellulose, as well as blends, derivatives, copolymers, and combinations thereof.

In the preferred embodiment, nanoparticles are formed of polylactide-co-glycolide, wherein the ratio of lactide to glycolide provides the desired degradation profile.

As demonstrated by the examples, PLGA nanoparticles can be synthesized using a single-emulsion, solvent evaporation technique. The solvent should dissolve both the polymer and drug, but without damaging the drug. For example, dichloromethane (DCM) was chosen as the solvent due to its ability to dissolve a wide range of hydrophobic drugs. Typically a ratio equivalent to about 2 ml solvent to 100 mg polymer is used.

The particles are made using GRAS solvents such as ethyl acetate, as described in the examples. Additives include trehalose or other sugars or aggregation-reducing materials. Trehalose is the best. Other sugars include glucose, sucrose and lactose. Typically, the weight ratio of sugar to nanoparticles is between 10-50%.

B. Therapeutic, Diagnostic and Prophylactic Agents

In the preferred embodiment, drugs that have already been approved for clinical use are screened for delivery and efficacy in treatment of the cns, especially brain tumors such as glioblastomas, as described in the examples.

Representative therapeutic agents include vascular endothelial growth factor ("VEGF") or VEGF receptor inhibitors such as bevacizumab, alkylating agents such as temozolomide or BCNU (carmustine), and other antineoplastics such as procarbazine. Preferred compounds include Carmustine (BCNU), temozolomide, taxols such as paclitaxel, camptothecin, and dithiazanine iodide (DI). The particles can also be used to deliver short acting radioactive compounds.

Loading can range from 0.1 to 20%, with more typical values between 1-10%

Prophylactics can include compounds alleviating swelling, reducing radiation damage, and anti-inflammatories.

Diagnostic agents can be radioactive, magnetic, or x-ray or ultrasound-detectable.

III. Method of Manufacture

In a preferred embodiment, a partial centrifugation technique is used to produce particles of the desired diameter. The polymer and drug are dissolved in a common solvent then added to an emulsifying solvent, i.e., one that is more water soluble or hydrophilic such as polyvinyl alcohol Other emulsifying solvents, including didodecyl dimethyl ammonium bromide (DMAB) and Pluronic F68, can be used. Using a solvent such as DMAB solution as the emulsifying solvent may result in even smaller nanoparticles. However, PVA has the least toxicity among these surfactants. After solvent evaporation and prior to particle washing, the particle solution is subjected to low-speed centrifugation, for example, 8,000 g for 10 min, which causes larger particles to pellet while keeping the smaller particles in the supernatant. The initial pellet contains comparatively large nanoparticles and is discarded. Nanoparticles in the supernatant are collected and washed using high-speed centrifugation, for example, 100,000 g for 30 min.

As demonstrated in the examples, scanning electron microscopy (SEM) showed that nanoparticles isolated using this protocol with dicloromethane (DCM) and PLGA were 74±18 nm in diameter and morphologically spherical. The typical yield for this fabrication was 12%±2%. In comparison, nanoparticles made using the same materials but with conventional centrifugation techniques were 150±30 nm in diameter, with an average yield of 55%±5%.

In a preferred embodiment, demonstrated by the examples, a partially water soluble solvent was used that provided enhanced results. Organic solvents used for preparing polymer solution are known to affect the size of PLGA nanoparticles synthesized through emulsion procedures. In particular, partially water-miscible organic solvents, such as benzyl alcohol, butyl lactate, and ethyl acetate (EA), allow nanoparticle formulation through an emulsion-diffusion mechanism and are able to produce smaller nanoparticles than water-immiscible solvents such as DCM. Using partially water-miscible organic solvents improves the yield of brain-penetrating nanoparticles. EA was chosen because of its low toxicity. Representative solvents that can be used include DCM, EA, benzyl alcohol, butyl lactate, and ethyl acetate (EA), acetone. Centrifugation parameters are the same for all solvents.

Lyophilization is used to stabilize nanoparticles for long-term storage. To reduce aggregation, a sugar such as the FDA-approved disaccharide trehalose is added to the particles at a ratio of 0.5:1 (trehalose:nanoparticles) by mass immediately prior to lyophilization.

IV. Method of Selection of Therapeutic Agents

Drug screening is initially performed in vitro then results confirmed in vivo.

Drug screening is performed in 96 well plates for primary screening. In a first embodiment, a slightly modified MTT assay is used to quantify the effects of drugs on cell proliferation, as described in the examples. Proliferation is also assessed and $IC_{50}$ calculated using a technique such as AlamarBlue (Invitrogen) fluorescence. Fluorescence measures were corrected for background media and drug fluorescence and normalized to the mean of vehicle measures. $IC_{50}$ values are determined using four-parameter logistic modeling using normalized point estimates.

A sphere formation assay plates brain stem cells as single-cell suspensions of 5 cells per μL in 48-well plates (Falcon). Cells are treated with 1 μM drug or equivalent concentration of DMSO. Growth factor is supplemented on day 5. Wells are counted on day 7. Colonies containing more than 5 cells are considered to be spheres. Percent inhibition is calculated as: (Control # spheres−Sample # spheres)/Control # spheres. At 3 days after plating, suspensions are collected and flow cytometry performed.

To establish tumors for evaluation of drug-loaded nanoparticles, tumor cells are injected into the brains of nude rats. Treatments are performed 7 days following tumor inoculation. 20 μL of either nanoparticles (100 mg/mL) or equivalent free drug are infused continuously. The animals' weight, grooming, and general health are monitored on a daily basis.

V. Method of Treatment

The particles are preferably administered into or adjacent to the area of the CNS to be treated. This may be at the time of or immediately after surgical resection of a tumor. Preferably, the particles are administered by injection into the tissue or the blood vessels leading into the brain. Particles can be introduced directly in the brain tissue by direct infusion or convection-enhanced delivery (CED). Alternately, they can be administered intravenously, or intra-arterially via catheter into an artery that serves the region of the brain to be treated.

To overcome the challenges associated with drug delivery to the brain or other regions of the central nervous system, a controlled-release delivery system comprised of brain-penetrating polymeric nanoparticles that can penetrate to substantially (~7-fold) higher volumes than conventional polymer nanoparticles when delivered intracranially using CED. The penetration of these particles is as good as any previously reported nanoparticle systems: for example, the $V_d/V_i$ achieved in the examples are comparable to those achieved with nanoliposomal delivery systems in rats. Polymeric particles have many advantages over liposomal formulations including lower toxicity and control of drug release. PLGA nanoparticles delivered in pig brains using CED penetrated to volumes of approximately 1180 $mm^3$. Since the vast majority of GBMs recur within 2 cm of the original tumor focus, the penetrative capacity of these brain-penetrating nanoparticles when delivered by CED can address the infiltrative nature of GBM. Surface-modified nanoparticles with [$^{18}$F]NPB4 using streptavidin-biotin conjugation, allows tracking the nanoparticles during the CED procedure using non-invasive PET imaging. This allows clinicians to visualize nanoparticles delivered by CED and ensure distribution of the therapeutic agent throughout the brain regions most likely in need of treatment.

In comparison to currently available nanocarrier drug delivery systems, this platform has at least three clear advantages. First, the polymer has an excellent safety profile: PLGA was approved by the Food and Drug Administration (FDA) in 1969 and has safely been used in clinics since that time. Second, the release kinetics of PLGA nanoparticles can be more easily modulated than those of competing nanocarrier systems utilized in intracranial applications, namely liposomes and micelles. Third, the versatile surface modification approach described in this study enables rapid, modular attachment of biotinylated agents, thereby allowing for efficient labeling of nanoparticles with a host of cell-targeting and -penetrating agents. Finally, the exceptionally small diameters allow these nanoparticles to penetrate relatively large, clinically relevant volumes when delivered by CED. In short, this is a versatile delivery platform for the CNS.

This delivery platform allows for the direct, rapid testing of new agents for treating GBM. BCSC resistance to conventional chemotherapeutics is a major challenge in GBM. A library screening approach to identify agents that have improved activity against BCSCs allowed screening of over 2,000 compounds. Based on these results, DI was selected for initial testing due to its abilities to inhibit growth, inhibit self-renewal, and encourage differentiation of cells it fails to kill. Brain-penetrating, DI-loaded PLGA nanoparticles inhibit tumor growth in an animal model that closely reflects many aspects of human GBM.

Although the brain-penetrating PLGA nanoparticle delivery vehicle was evaluated here against intracranial tumors with small molecule drugs, the system can be tailored for application to a host of CNS diseases. For example, surface modification or size fractionation could produce particles well suited for the treatment of neurodegenerative disorders. Additionally, these particles have the potential to encapsulate not only hydrophobic drugs but also a variety of nucleic acids for gene therapy applications. Due to their ability to penetrate brain tissue, their construction from safe components, the ability to control agent release, and the capacity to modulate particle surface chemistry, we anticipate that this brain-penetrating PLGA nanoparticle delivery platform will have significant clinical impact.

The present invention will be further understood by reference to the following non-limiting examples. The following materials and methods were used in the examples.

Chemicals

All chemicals were purchased from Sigma-Aldrich unless otherwise noted.

Cell Culture

Human glioma cell line U87MG was purchased from ATCC (American Type Culture Collection). Cells were grown at 37° C. incubator containing 5% CO2 and cultured in DMEM medium (Invitrogen) supplemented with 10% fetal bovine serum (Invitrogen), 100 units/mL penicillin and 100 μg/mL streptomycin (Invitrogen).

Primary Tumor Cultures from Human GBM Tissue

All studies were approved by the appropriate Institutional Review Boards. Tumor samples classified as GBM based on World Health Organization (WHO) criteria were obtained from neurosurgical patients at Yale-New Haven Hospital who had provided informed consent. Within 1 to 3 h of surgical removal, tumors were washed, cut into less than 1 mm³ fragments, and enzymatically dissociated into single cells. Digested fragments were filtered using a 70 μm cell strainer (BD Falcon) and collected in culture medium. The GS5 cell line was provided by Lamszus lab and described by Gunther et al., *Oncogene* 27, 2897-2909 (2008). All primary tumor cells were collected and cultured in Neurobasal A medium (Invitrogen) supplemented with B27 (Invitrogen), fibroblast growth factor-2 (20 ng/mL, Peprotech), and epidermal growth factor (20 ng/mL, Peprotech). Growth factors were added at least weekly.

Brain-Penetrating Nanoparticle Synthesis

Nanoparticles loaded with C6 or paclitaxel were synthesized by a single-emulsion solvent evaporation technique. 100 mg PLGA (50:50, Polysciences and Birmingham) and agents to be encapsulated were dissolved in 2 mL dichloromethane (DCM) or ethyl acetate (EA). The polymer/drug solution was then added dropwise to 4 mL of 2.5% polyvinyl alcohol (PVA) as the outer aqueous phase and sonicated to form an emulsion. The emulsion was poured into a beaker containing aqueous 0.3% (v/v) PVA and stirred at room temperature for 3 h (DCM as solvent) or 5 h (EA as solvent) to allow the solvent to evaporate and particles to harden.

To synthesize standard nanoparticles, following the solvent evaporation phase, the nanoparticle solution was subjected to typical centrifugation speeds (11,500×g for 15 min, ×3) and the pellet was collected. To synthesize brain-penetrating nanoparticles, following the solvent evaporation phase, the nanoparticle solution was first centrifuged at low speed (8,000×g for 10 min) to pellet the large particles. The supernatant was decanted and brain-penetrating nanoparticles were collected through high-speed ultracentrifugation (100,000×g for 30 min, ×2).

As used herein, large nanoparticles synthesized using standard protocol are between about 120-200 nm. Brain penetrating nanoparticles for tumor treatment are between about 60 and 90 nm and for normal brain tissue are less than 90 nm To prevent nanoparticle aggregation during lyophilization, trehalose was added to the final aqueous solution at a ratio of 0.5:1 (trehalose:nanoparticles) by mass immediately prior to lyophilization.

Scanning Electron Microscopy (SEM)

Particle size was characterized by scanning electron microscopy (SEM). Samples were mounted on carbon tape and sputter-coated under vacuum with gold in an argon atmosphere using a Dynavac Mini Coater set at 40 mA current (Dynavac, USA). SEM was carried out using a Philips XL30 SEM and LaB electron gun with an accelerating voltage of 3 kV. Mean particle diameters and size distributions were determined by image analysis of approximately 200 particles using ImageJ (National Institutes of Health). The same images were used to qualitatively assess particle morphology.

Characterization of Nanoparticle Loading

To determine the loading and encapsulation efficiency of C6 nanoparticles, 3-5 mg nanoparticles were dissolved in 1 mL DMSO at room temperature. Loading of C6 in the nanoparticles was quantified based on the solution's fluorescence intensity (ex: 444 nm, em: 538 nm) using a spectrophotometer (Spectromax M5, Molecular Devices). Blank nanoparticles were used for background control. Paclitaxel loading was quantified using HPLC. The same approach was used to characterize loading of DI in nanoparticles, except that the concentration of DI was determined based on its absorbance at 655 nm.

In Vitro Controlled Release

Nanoparticles (3-5 mg) were suspended in 1 mL PBS (pH 7.4), and incubated at 37° C. with gentle shaking (70 rpm). Release of C6, paclitaxel, or DI was monitored at several time points over a 4-week period. At each sampling time, the nanoparticle suspension was centrifuged for 15 min at 15,000 rpm. The supernatant was removed for quantification of C6, paclitaxel, or DI and replaced with an equivalent volume of PBS for continued monitoring of release. Detection of C6, paclitaxel, or DI was conducted using the methods described above.

Fluorescence-Based Imaging of Nanoparticle Distribution in Rat Brain

All procedures involving animals were approved by the Yale University Institutional Animal Care and Utilization Committee (IACUC). Female athymic (NCr-nu/nu) nude rats were maintained in a sterile environment. Rats were anesthetized with ketamine/xylazine solution via intraperitoneal injection and given analgesic. The scalp was prepared for surgery with betadine and alcohol. The rat was then placed in a stereotactic head frame. A midline incision was made and a 1.5 mm diameter hole was drilled in the skull 3 mm lateral and 0.5 mm anterior to the bregma. A 26G Hamilton syringe, with 28G stepdown inner cannula, was inserted to a depth of 5 mm. The tissue was allowed to equilibrate mechanically for 5 min. Subsequently, 20 μL of nanoparticles or free drug was infused ($V_1$) continuously at a rate of 0.667 μL/min. Following infusion, the syringe was left in place for 5 min to allow for equilibration. For delivery studies, animals were sacrificed 30 min post-infusion; the brains were harvested and frozen.

Nanoparticle distribution was quantified as described by Neeves, et al *Brain Res* 1180, 121-132 (2007). Each brain was serially sectioned into 150 μm slices on a cryostat. The distribution of nanoparticles in the slices was captured on a fluorescent stereoscope (Zeiss Lumar V.12, Carl Zeiss, Thornwood, N.Y.) using a CY3 filter. The exposure time was optimized to achieve maximum dynamic range at the infusion site while simultaneously avoiding saturation. Exposure time for each nanoparticle group was individually optimized, in order to adjust for differences in loading between nanoparticle groups. Within each group of nanoparticles, the exposure time was held constant. The distribution volume ($V_d$) of the nanoparticles was calculated using a custom Matlab 7.2 (MathWorks, Natick, Mass.) script, which generated a binary image from the greyscale images and calculated the area of particle penetration. The threshold for the binary operation was 10% of the maximum fluorescent intensity. The total $V_d$ was calculated by multiplying the distribution area in each slice by the slice thickness (150 μm) and summing the volumes of all slices.

Synthesis of [$^{18}$F]NPB4 Nanoparticles

[$^{18}$F]NPB4 was prepared as described by Zheng et al., *J. Nuclear Medicine* 52, 417 (2011), with 28%±14% radiochemical yield, >98% radiochemical purity, and 1-2 mCi/nmol specific activity. In preliminary experiments, [$^{18}$F]NPB4 was conjugated to avidin surface-modified PLGA nanoparticles by incubating 7 mg of nanoparticles with approximately 0.6 mCi of [$^{18}$F]NPB4 for 1 h at room temperature. When this solution was centrifuged to pellet the nanoparticles, no radioactivity was detected in the wash. Less than 1% of the total added radioactivity was detected in the wash. It was estimated that <1% of available avidin sites on the nanoparticles were occupied by the [$^{18}$F]NPB4. Each rat received a total dose of 100-300 uCi.

PET-Based Imaging of Nanoparticle Distribution in Rat Brain

For noninvasive imaging studies, Sprague Dawley rats were anesthetized with ketamine/xylazine and received a 26G guide cannula (Plastics One, Roanoke Va.) to enable nanoparticle infusions while data collection was ongoing. The guide cannula was secured to the surface of the skull with dental cement (Henry Schein) and surgical screws. Once in the scanner, rats were maintained on isoflurane anesthesia (2%), and an infusion needle was threaded through the cannula to the target brain region. Emission data were collected during the infusion and for 30 min after completion with a Focus 220 small animal PET scanner (Siemans, Medical Solutions, Knoxville, Tenn.). A transmission scan ($^{57}$Co source, 9 min) was collected prior to the emission scan. Rats were sacrificed immediately after the scan and frozen in liquid nitrogen for later tissue sectioning and fluorescence microscopy. PET data were binned into 0.5-10 min frames and reconstructed with the ordered subset expectation maximization algorithm (OSEM), with corrections for attenuation, decay, randoms, and scatter. The resulting pixel size was 0.949×0.949×0.796 mm, with an effective image resolution of ~1.5 mm. Radial concentration profiles were extracted from each data frame and thresholded to 10% of the maximum value to determine the spatial volume of distribution.

Fluorescence-Based Imaging of Nanoparticle Distribution in Pig Brain

Nanoparticle infusions were performed in the striatum of Yorkshire pigs to evaluate $V_d$ in a large animal model. Pigs were anesthetized with ketamine/xylazine, intubated, and maintained with isofluorane/oxygen/$NO_2$. The head was positioned such that the horizontal zero plane passed through bregma and was parallel to a line between the upper margin of the infraorbital ridge and the upper margin of the external auditory meatus. The scalp was prepped with betadine and alcohol. A linear midline incision was made and a 1.5 mm diameter hole was drilled in the skull 11 mm lateral to bregma. A 26G Hamilton syringe, with 28G stepdown inner cannula, was inserted to a depth of 28 mm. The tissue was allowed to equilibrate mechanically for 5 min. Subsequently, 337.5 μL of nanoparticle solution were continuously infused at a rate of 0.5 μL/min for 30 min, 0.75 μL/min for 30 min, and 1 μL/min for 300 min. Following infusion, the syringe was left in place for 120 min, after which it was removed. Animals were subsequently sacrificed; the brains were harvested, frozen, and sectioned as described above. Nanoparticle distribution was quantified using the methods described above. Exposure time was held constant between all animals.

Drug Screening

Drug screening was performed in clear 96 well plates using a compound library which contains 1,937 compounds that are or were FDA-approved as reported by Chong, et al. *Nature chemical biology* 2, 415-416 (2006).

Cell Proliferation Assays

For primary screening, a slightly modified MTT assay was used to quantify the effects of drugs on cell proliferation. Briefly, cells were cultured in 96-well plates (Falcon). Three (for BCSC studies) or six (for U87MG studies) days after treatment, medium was removed and replaced with fresh medium containing 10% MTT (3-(4,5-dimethylthiazol-2-yl)-2,5-diphenyl tetrazolium bromide) (Sigma) solution (4.14 mg/mL). Four hours after incubation at 37° C., all media was removed. Formazan was dissolved in DMSO and the optical density (O.D.) was measured at 590 nm. The relative inhibition on growth was determined using the following formula: Growth inhibition=(control O.D.−sample O.D.)/control O.D.

Proliferation was also assessed and $IC_{50}$ calculated using AlamarBlue (Invitrogen) fluorescence. Briefly, cells were plated at subconfluent concentration in black clear-bottomed 96-well plates (Falcon) with drug concentrations spanning eight orders of magnitude. Three or six days post-plating (as above), AlamarBlue was added at manufacturer's recommended concentration. Cells were incubated at 37° C. for 200 min and quantified (ex: 544 nm, em: 590 nm). Fluorescence measures were corrected for background media and drug fluorescence and normalized to the mean of vehicle measures. $IC_{50}$ values were determined using four-parameter logistic modeling using normalized point estimates.

Sphere Formation Assay

BCSCs were plated as single-cell suspensions of 5 cells per μL in 48-well plates (Falcon). Cells were treated with 1 μM drug or equivalent concentration of DMSO. Growth factor was supplemented on day 5. Wells were counted on day 7. Colonies containing more than 5 cells were considered to be spheres. Percent inhibition was calculated as: (Control # spheres−Sample # spheres)/Control # spheres.

Flow Cytometry

BCSCs were plated as single-cell suspensions in 6-well plates with 100 nM drug or DMSO. At 3 days after plating, suspensions were collected and flow cytometry performed. Briefly, following reconstitution in 0.5% BSA in PBS (w/v), dissociated cells were washed in cold PBS and subsequently incubated with biotin-conjugated anti-CD133 (PROM1) antibody (Miltenyi Biosciences). Suspensions were incubated with avidin-conjugated AlexaFluor 488 (Invitrogen) and read on a BD FACSCAN flow cytometer (BD Biosciences). Geometric means were calculated in FlowJo (TreeStar, Inc.), corrected for background (secondary only), and normalized to DMSO-only treated cells.

Antitumor Activity in Xenograft Model

To establish tumors for evaluation of paclitaxel-loaded PLGA nanoparticles, nude rats were first anesthetized with a ketamine/xylazine mixture. Animals were then prepped with betadine and alcohol and placed in a stereotactic frame. A linear midline incision was made and a 1.5 mm diameter hole was drilled in the skull 3 mm lateral and 0.5 mm anterior to bregma. A 26G Hamilton syringe was inserted to a depth of 5 mm. The tissue was allowed to equilibrate mechanically for 5 min. Subsequently, $5 \times 10^5$ U87MG cells in 2 μl PBS was injected into the brain at a rate of 0.5 μl/min. The burr hole was filled with bone wax (Lukens, Reading Pa.), the scalp closed with surgical staples, and the rat removed to a clean cage with free access to food and water mixed with ibuprofen. Treatments were performed 7 days following tumor inoculation. Rats were again anesthetized, prepped, and placed in a stereotactic frame. The wound was reopened and the Hamilton syringe was oriented as described previously. 20 μL of either nanoparticles (100 mg/mL) or equivalent free drug were infused continuously at a rate of 0.667 μL/min. Following infusion, the syringe was left in place for 5 min, after which it was removed. The burr hole was filled with bone wax (Lukens, Reading Pa.), the scalp closed with surgical staples, and the rat removed to a clean cage with free access to food and water mixed with ibuprofen. The animals' weight, grooming, and general health were monitored on a daily basis. Animals were euthanized after either a 15% loss in body weight or when it was humanely necessary due to clinical symptoms. The same procedures were used to evaluate DI nanoparticles, except that GS5 cells were injected intracranially and treatment was performed 10 days following tumor cell inoculation.

Statistical Analysis

All data were collected in triplicate, unless otherwise noted, and reported as mean and standard deviation. Comparison of two conditions was evaluated by a paired Student's t-test. Kaplan-Meier analysis was employed to evaluate the effect of various treatments on survival. A $p<0.05$ was considered to indicate a statistically significant difference.

Example 1: Synthesis of Brain-Penetrating PLGA Nanoparticles

Materials and Methods

PLGA nanoparticles were synthesized using a single-emulsion, solvent evaporation technique. Dichloromethane (DCM) was chosen initially as the solvent due to its ability to dissolve a wide range of hydrophobic drugs. A partial centrifugation technique was used to produce particles of the desired diameter. Specifically, after solvent evaporation and prior to particle washing, the particle solution was subjected to low-speed centrifugation (8,000 g for 10 min), which caused larger particles to pellet while keeping the smaller particles in the supernatant. The initial pellet contained comparatively large nanoparticles and was removed. Nanoparticles in the supernatant were collected and washed using high-speed centrifugation (100,000 g for 30 min).

Results

Scanning electron microscopy (SEM) showed that nanoparticles isolated using this protocol were 74±18 nm in diameter and morphologically spherical. The typical yield for this fabrication was 12%±2%. In comparison, nanoparticles made using the same materials but with conventional centrifugation techniques were 150±30 nm in diameter, with an average yield of 55%±5%.

Example 2: Synthesis of Brain Penetrating NPs with Water-Miscible Solvent

Materials and Methods

Partially water-miscible organic solvents, such as benzyl alcohol, butyl lactate, and ethyl acetate (EA), allow nanoparticle formulation through an emulsion-diffusion mechanism and are able to produce smaller nanoparticles than water-immiscible solvents such as DCM. TEA was chosen because of its low toxicity. The same method otherwise was used as in Example 1.

Results

Nanoparticles synthesized using EA as solvent instead of DCM were 65±16 nm in diameter and morphologically spherical. The yield was improved with EA: 44%±3%.

Example 3: Cryoprotection of Brain-Penetrating PLGA Nanoparticles

Materials and Methods

Lyophilization is a technique commonly used to stabilize nanoparticles for long-term storage. However, lyophilization can also cause nanoparticles to aggregate, making them difficult to resuspend in an aqueous solution. Furthermore, particle aggregation, if it did occur, could complicate CED infusion and restrict penetration in the brain. To reduce aggregation, the FDA-approved disaccharide trehalose was added as an excipient, at a ratio of 0.5:1 (trehalose:nanoparticles) by mass immediately prior to lyophilization.

Results

The addition of trehalose did not alter nanoparticle size, morphology, or yield. SEM images demonstrated that trehalose enhanced the separation of nanoparticles from one another when compared to nanoparticles lyophilized without trehalose. Reconstitution of cryoprotected brain-penetrating nanoparticles resulted in a homogenous solution, while reconstitution of nanoparticles lyophilized without trehalose cryoprotection resulted in sedimentation over time, which caused clogging of the CED device and prevented infusion at a consistent pressure.

Example 4: CED of Brain-Penetrating PLGA Nanoparticles in the Rat Brain

Materials and Methods

The effects of particle size and cryoprotection on intracranial CED and volume of distribution ($V_d$) was assessed for both brain-penetrating PLGA nanoparticles and standard PLGA nanoparticles. Prior to lyophilization, nanoparticles from each group were further divided into two groups: with or without trehalose cryoprotection. Nanoparticles were loaded with coumarin-6 (C6), a fluorescent dye commonly used for visualization. Brain-penetrating and standard nanoparticles had mean diameters of 71 nm±13 nm and 147 nm±27 nm, respectively. Consistent with previous work (44), release of C6 from nanoparticles was negligible (<0.5%) at 72 h.

Sixteen nude rats received 20 µL infusions ($V_i$) of C6-loaded nanoparticles into the right striatum via CED (n=4 per group). Animals were sacrificed 30 min after infusion and their brains were sectioned and analyzed using fluorescence microscopy to determine $V_d$.

Results

Both small size and trehalose cryoprotection independently contributed to increased penetrance of nanoparticles in brain parenchyma. Brain-penetrating nanoparticles with cryoprotectant resulted in the best distribution in the brain. Mean $V_d$ for brain-penetrating particles with trehalose was 74 mm³±7 mm³ ($V_d/V_i$=3.7±0.3) while mean $V_d$ for standard particles without trehalose was 11 mm³±3 mm³ ($V_d/V_i$=0.6±0.1), p<0.05. For brain-penetrating nanoparticles with trehalose, the $V_d/V_i$ approaches the theoretical limit of 5, which is usually only achievable by ideal free drugs in solution.

Example 5: Live, Non-Invasive Imaging of Brain-Penetrating Nanoparticles in the Rat Brain Using PET Materials and Methods The clinical translation of delivery systems for the treatment of intracranial diseases has been hindered by an inability to non-invasively characterize in vivo distribution. A modular radiolabeling strategy was employed to permit noninvasive, quantitative PET imaging of the brain-penetrating nanoparticles. PLGA nanoparticles were modified to display surface-bound palmitylated avidin, which enabled facile radiolabeling of nanoparticles with N-(4-[$^{18}$F]fluorobenzyl)propanamido-PEG$_4$-Biotin ([$^{18}$F]NPB4), a biotinylated, gamma-emitting compound that can be detected with PET. [$^{18}$F]NPB4-labeled and C6-loaded PLGA nanoparticles were synthesized and delivered via CED to the right striatum of five Sprague-Dawley rats. Three rats received infusions of brain-penetrating PLGA nanoparticles with trehalose, while the other two rats received infusions of standard nanoparticles without trehalose ($V_i$=20 µL for both groups).

Results

When measured noninvasively and quantitatively with PET imaging, the mean $V_d$ for the brain-penetrating nanoparticles was 111±3 mm³ ($V_d/V_i$=5.5±0.2), while the mean $V_d$ for the standard nanoparticles was 53±23 mm³ ($V_d/V_i$=2.6±1.2). Post-mortem analysis using fluorescence microscopy revealed that the mean $V_d$ for the brain-penetrating nanoparticles was 82 mm³±5 mm³ ($V_d/V_i$=4.1±0.2), while the mean $V_d$ for the standard nanoparticles was 11 mm³±4 mm³ ($V_d/V_i$=0.5±0.2). Thus, consistent with imaging results from destructive fluorescence microscopy, quantitative analysis of non-invasive PET imaging demonstrated that brain-penetrating nanoparticles reached a larger volume of spatial distribution than standard nanoparticles.

Example 6: CED of Brain-Penetrating Nanoparticles in the Pig Brain

Materials and Methods

Rodent brains are much smaller than human brains, so it is difficult to assess whether the $V_d$ obtained after CED in the rat is relevant to treatment of human disease. To extend the analysis to larger brains, brain-penetrating, C6-loaded PLGA nanoparticles were infused into the striatum of pig brains (n=4) using the CED technique ($V_i$=338 uL). Animals were sacrificed 120 min post-infusion and their brains were analyzed with fluorescence microscopy to determine $V_d$.

Results

Brain-penetrating PLGA nanoparticles delivered by CED penetrated pig brain tissue with a mean $V_d$ of 1180 mm³±37 mm³, which resulted in $V_d/V_i$=3.5±0.1, similar to the value obtained in the rat and again approaching the theoretical limit of 5. The extent of nanoparticle penetration in the pig brain was >1 cm. The brain-penetrating nanoparticles can be administered over volumes that are clinically relevant, since the vast majority of GBMs recur within 2 cm of their original location. Even greater penetration is possible in humans, since infusion volumes of up to 72 mL have been used safely in previous clinical trials.

Example 7: Delivery of Chemotherapy for Solid Brain Tumor

Materials and Methods

Whether these brain-penetrating PLGA nanoparticles could be used to treat intracranial tumors was assessed. For initial studies, intracranial tumors in immunocompromised rats were established by injection of U87MG, a widely-used, non-BCSC human GBM cell line, and animals treated with CED of paclitaxel, a drug previously shown to inhibit proliferation of U87MG. PLGA nanoparticles loaded with paclitaxel were synthesized by two techniques: brain-penetrating and standard paclitaxel-loaded nanoparticles were spherical and of expected diameters (75±20 nm and 159±38 nm, respectively). All nanoparticle fabrications (brain-penetrating and standard) were loaded with paclitaxel, having encapsulation efficiencies of approximately 60%, and yields of greater than 35%.

Figure 1B:
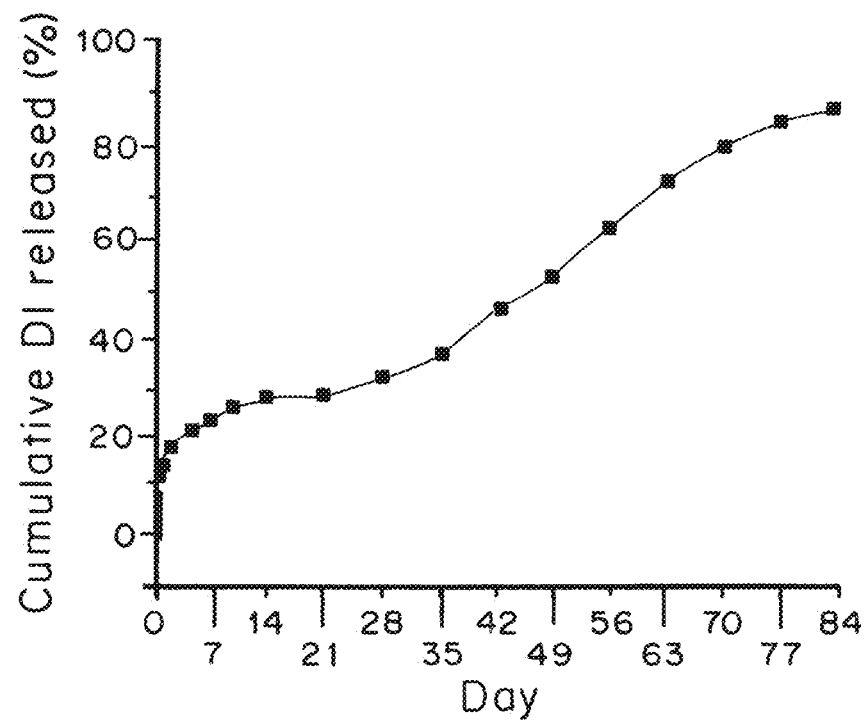

Controlled release experiments showed that brain-penetrating and standard PLGA nanoparticles released paclitaxel similarly, with approximately 75% of the encapsulated drug released from each formulation over the first 28 days of incubation. See FIG. 1A. Both brain-penetrating and standard paclitaxel nanoparticles inhibited growth of U87MG in vitro, exhibiting lower IC$_{50}$s (39 nM and 37 nM, respectively) than free drug (169 nM). None of the blank nanoparticle formulations exhibited cytotoxicity. See FIG. 1B.

Figure 1C:
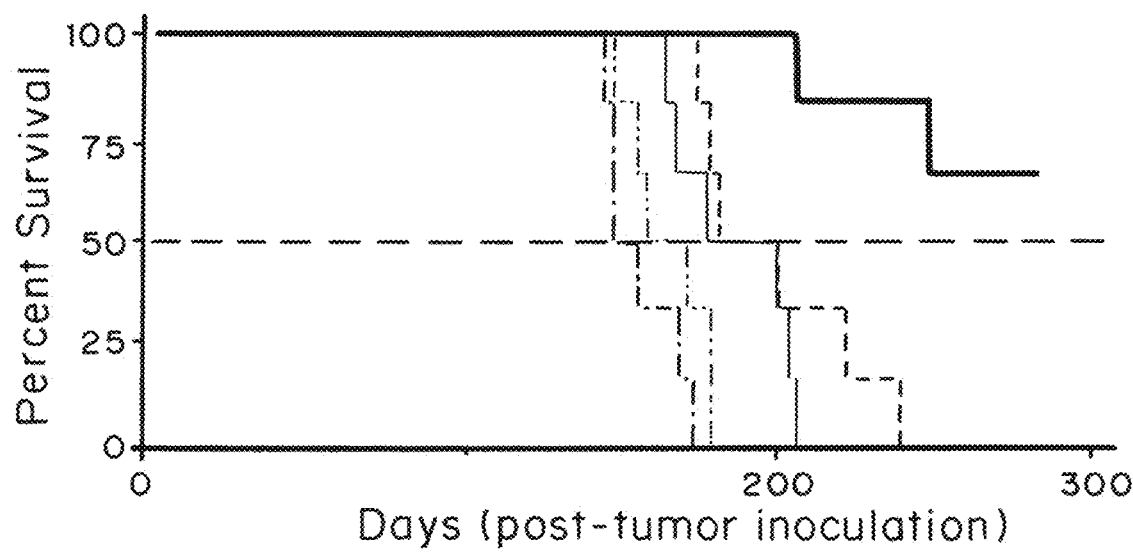

To determine in vivo efficacy, U87MG-derived xenografts were generated in the right striatum of nude rats. Tumor-bearing rats were divided into five groups that received either no treatment; CED of brain-penetrating, paclitaxel-loaded nanoparticles; CED of standard, paclitaxel-loaded nanoparticles; CED of blank, brain-penetrating nanoparticles; or CED of paclitaxel in solution. Consistent with previous experience, rats tolerated all procedures well; no periprocedural toxicity was observed in any of the treatment groups. Rats were further monitored for survival: blank nanoparticles and free paclitaxel failed to show a survival benefit when compared to no treatment. Kaplan-Meier analysis revealed that rats treated with brain-penetrating, paclitaxel-loaded nanoparticles had significant improvements in median survival (46 days) when compared to all groups (standard nanoparticles: 38 days, free drug: 30 days, blank/unloaded nanoparticles: 31 days, no treatment: 27 days; $p<0.05$). See FIG. 1C.

Example 8: Identification of Novel Small Molecules that Inhibit BCSC Proliferation and Self-Renewal Materials and Methods A histopathologic hallmark of GBM is its infiltrative nature. The U87MG cell line has been propagated in cell culture for many years and has lost its infiltrative nature in vivo. After intracranial injection, U87MG cells form solid tumors that are histopathologically distinct from human GBM. In contrast, several recent studies have demonstrated that a murine xenograft model utilizing human BCSCs has the ability to precisely recapitulate human GBM histopathology. To test whether BCSCs were able to form such tumors in nude rats, GS5, a well-characterized BCSC line was inoculated in rat brains. Consistent with the findings in mouse brains, GS5 tumors in the brain of nude rats are highly infiltrative and histopathologically similar to human GBM.

Figure 3A:
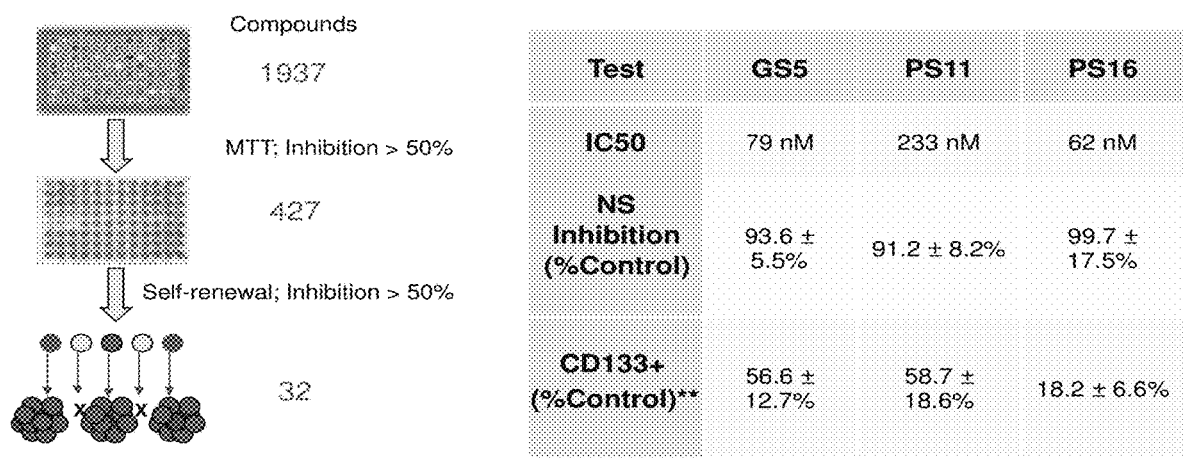

A library of approximately 2,000 compounds that at one time or another have been approved for use in humans by the FDA for growth-inhibitory activity was screened against GS5. Briefly, GS5 cells were plated in 96-well format, treated with 5 µM drug, and evaluated for viability three days later using the Thiazolyl Blue Tetrazolium Bromide (MTT) assay. Initial hits were subsequently evaluated for inhibition of GS5 sphere formation, a measure of BCSC self-renewal. Thirty-two candidate compounds were identified (FIGS. 3A, 3B), some of which were later confirmed in an independent high-throughput screen in BCSCs. The BCSC growth-inhibiting activity of many compounds was confirmed using AlamarBlue.

One compound in particular, the anti-helminthic cyanine dye dithiazanine iodide (DI), potently inhibited GS5 proliferation, with an $IC_{50}$ of 79 nM. DI inhibited GS5 sphere formation, a measure of BCSC self-renewal, by 94%. Additionally, DI decreased the CD133+ cell population by 57% in DI treated culture. DI was evaluated in two additional BCSC lines, PS11 and PS16, and showed similar anti-BCSC effects.

Example 9: CED of Brain-Penetrating, DI-Loaded PLGA Nanoparticles for GBM Therapy Materials and Methods CED of brain-penetrating, DI-loaded nanoparticles was tested to see if it could prevent the growth of a more histopathologically relevant model of GBM than U87MG. DI was loaded into brain-penetrating nanoparticles with encapsulation efficiency of 19% and yield of 18%. Brain-penetrating, DI-loaded nanoparticles were spherical and had an average diameter of 70±19 nm. DI was released from brain-penetrating nanoparticles in a controlled manner over several weeks. To evaluate their efficacy in vivo, brain-penetrating, DI-loaded nanoparticles were administered via a single infusion into rat brains bearing GS5-derived tumors.

Results

DI nanoparticles significantly increased survival of tumor-bearing rats. The median survival for control rats receiving either no treatment or blank nanoparticles was 115 and 113 days, respectively. In contrast, only one rat in the DI nanoparticle treatment group exhibited neurological symptoms and was euthanized 189 days after treatment, while the other five rats in the DI group remained healthy for over 250 days.

Figure 2A:
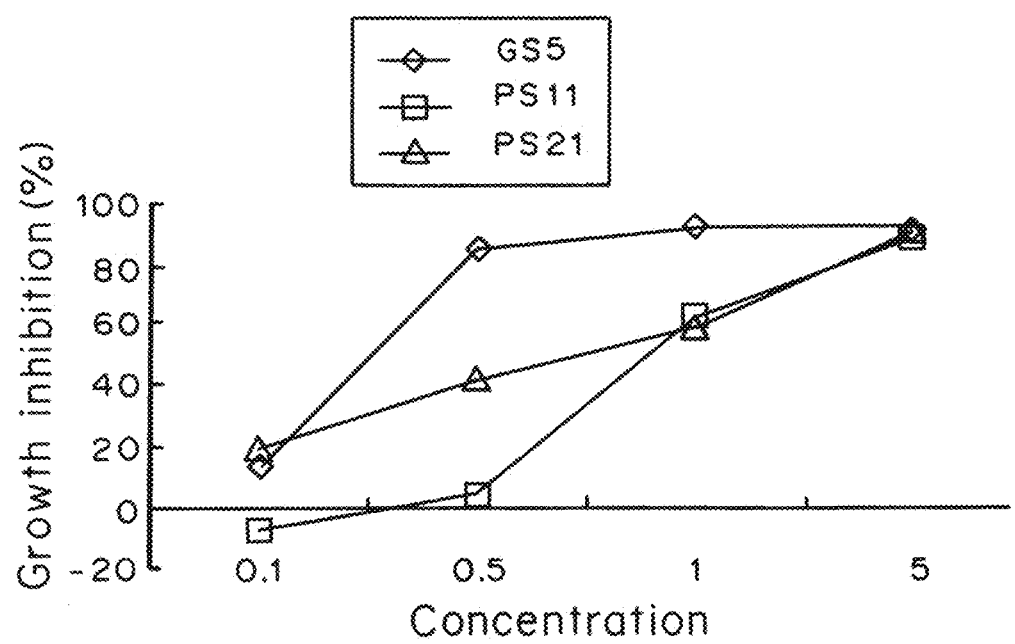
FIGS. 2A-2C are graphs evaluating the effects of digoxin on BCSCs in vitro and in vivo.
Figure 2B:
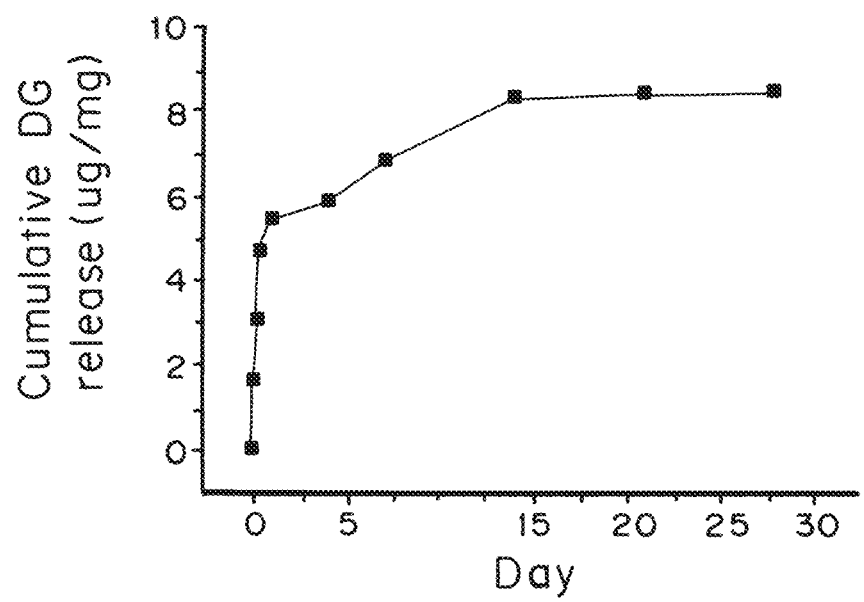
Figure 2C:
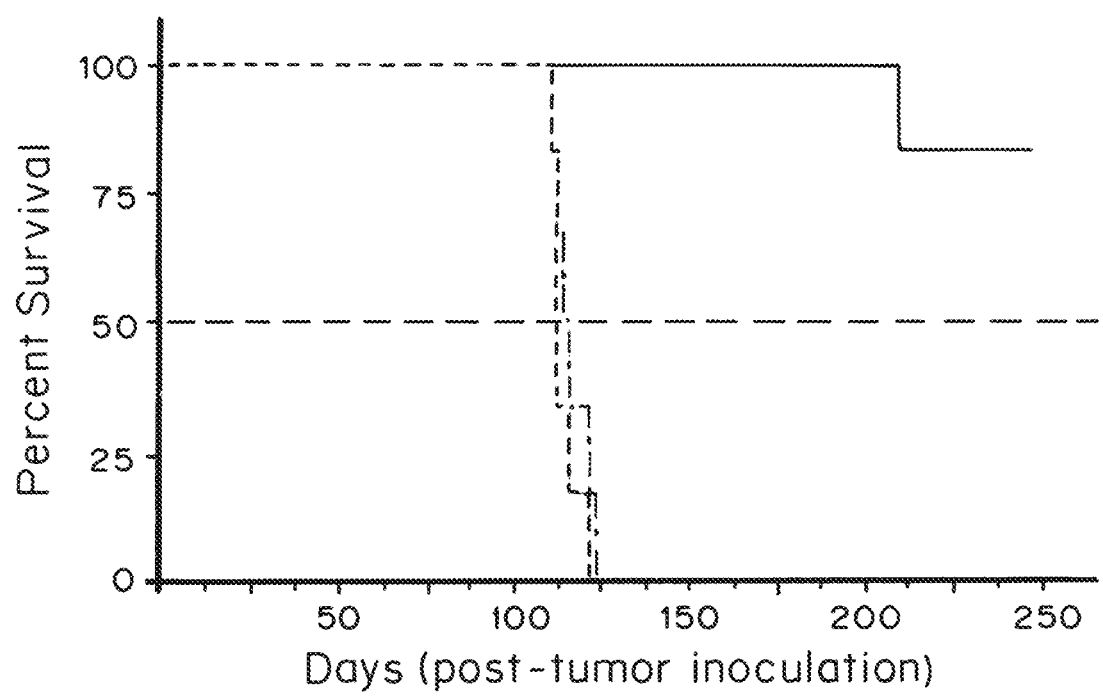

Example 10: Anisomycin and Digoxin Particles were not Effective Using CED Delivery Two other compounds that exhibited activity in the in vitro screening experiments were tested. Both anisomycin and digoxin performed well on in vitro assays against BCSCs and were loaded efficiently into brain-penetrating nanoparticles that provided controlled release. In pilot experiments, however, CED delivery of anisomycin-loaded or digoxin-loaded particles provided no survival benefit to rats with intracranial BCSC-derived tumors. See FIGS. 1C and 2C.

We claim:

1. A formulation comprising nanoparticles consisting of a core and shell which can be suspended in a pharmaceutically acceptable carrier for convection enhanced delivery (CED),
    wherein the core of the nanoparticles consist of biodegradable hydrophobic polymer selected from the group consisting of poly(lactic acid) (PLA), poly(lactic-co-glycolic acid) (PLGA), poly(lactic acid)-polyethyleneglycol (PLA-PEG) block copolymers, polyanhydrides, poly(ester anhydrides), polyglycolide (PGA), poly-3-hydroxybutyrate (PHB) and copolymers thereof, poly-4-hydroxybutyrate (P4HB), blends thereof and copolymers thereof, and a therapeutic, diagnostic, or prophylactic agent, and
    have an average diameter of between 25 and 100 nm, and
    wherein the shell is on the surface of the nanoparticle core and the shell comprises a pharmaceutically acceptable sugar selected from the group consisting of trehalose, glucose, sucrose and lactose in an amount of between 10 and 50% by mass of the nanoparticle, effective to increase penetration of the nanoparticles through brain tissue.

2. The formulation of claim 1 wherein the nanoparticles are formed by emulsification with a partially water-miscible solvent, which is removed from the nanoparticles.

3. The formulation of claim 1 wherein the sugar is trehalose and wherein the ratio of trehalose to nanoparticles is 0.5:1 (trehalose:nanoparticles) by mass.

4. The formulation of claim 1 wherein the agent is a chemotherapeutic for treatment of cancer.

5. The formulation of claim 4 wherein the agent is selected from the group consisting of Carmustine (BCNU), temozolomide, taxols, camptothecin, and dithiazanine iodide (DI).

6. A method of delivering a therapeutic, prophylactic or diagnostic agent to the central nervous system of a subject in need thereof comprising injecting or infusing by convection-enhanced delivery into the blood stream or tissue adjacent to the region of the central nervous system to be treated the formulation of claim 1.

7. The method of claim 6 wherein the particles can penetrate brain tissue and are between 25 and 90 nm average diameter.

8. The method of claim 7 wherein the particles are for treatment of brain tumors and have an average diameter of between 60 and 90 nm.

9. The method of claim 6 wherein the agent is a therapeutic in an amount effective to reduce the size or alleviate the symptoms of a brain tumor.

10. The method of claim 9 wherein the agent is selected from the group consisting of carmustine (BCNU), temozolomide, taxols, camptothecin, and dithiazanine iodide (DI).

11. The formulation of claim 1, wherein the sugar is selected from the group consisting of glucose, sucrose and lactose.

12. The formulation of claim 1 wherein the particles have a size of between 25 and 90 nm.

13. The formulation of claim 12, wherein the particles have a size of between 60 and 90 nm.

14. The formulation of claim 1, wherein the polymer is poly(lactic-co-glycolic acid) (PLGA), the agent is a chemotherapeutic, and the sugar is trehalose in an amount of between 10 and 50% of the weight of the biodegradable hydrophobic polymer, effective to increase penetration of the nanoparticles through brain tissue.

15. The formulation of claim 1, prepared by
  (i) subjecting a polymer/agent solution to single-emulsion solvent evaporation to form a nanoparticle solution,
  (ii) centrifuging the nanoparticle solution at a slow speed to form a first pellet and a first supernatant,
  (iii) discarding the first pellet and centrifuging the first supernatant at high speed to form the nanoparticles, and
  (iv) lyophilizing the nanoparticles with the sugar, to remove the solvent.

16. The formulation of claim 15, wherein the solvent is a partially water-miscible solvent.

17. The formulation of claim 1, wherein the sugar is trehalose.

* * * * *